United States Patent
Bertoni

(10) Patent No.: US 11,273,248 B2
(45) Date of Patent: Mar. 15, 2022

(54) METHOD TO DIVIDE LIPOSUCTION FAT INTO ALIQUOTS TO BE USED AND CRYOPRESERVED

(71) Applicant: Biomed Device S.R.L., Fraz. Cognento (IT)

(72) Inventor: Marco Bertoni, Fraz. Cognento (IT)

(73) Assignee: Biomed Device S.R.L., Modena (IT)

( * ) Notice: Subject to any disclaimer, the term of this patent is extended or adjusted under 35 U.S.C. 154(b) by 479 days.

(21) Appl. No.: 16/286,633

(22) Filed: Feb. 27, 2019

(65) Prior Publication Data

US 2019/0183113 A1     Jun. 20, 2019

Related U.S. Application Data

(63) Continuation of application No. 14/909,467, filed as application No. PCT/IB2014/063632 on Aug. 1, 2014, now abandoned.

(30) Foreign Application Priority Data

Aug. 2, 2013    (IT) .......................... MO2013A000228

(51) Int. Cl.
     *A61M 1/00*          (2006.01)
     *A61M 1/02*          (2006.01)
     (Continued)

(52) U.S. Cl.
     CPC ........... *A61M 1/892* (2021.05); *A01N 1/0257* (2013.01); *A01N 1/0284* (2013.01);
     (Continued)

(58) Field of Classification Search
     CPC .... A61M 1/0209; A61M 1/3695; A61M 1/89; A61M 1/892; A61M 1/893;
     (Continued)

(56) References Cited

U.S. PATENT DOCUMENTS

| | | | |
|---|---|---|---|
| 6,852,074 B1 | 2/2005 | Jorgenson et al. | |
| 2005/0008626 A1* | 1/2005 | Fraser | C12N 5/0667 424/93.21 |

(Continued)

FOREIGN PATENT DOCUMENTS

| | | |
|---|---|---|
| EP | 1930033 | 6/2008 |
| WO | WO 2006/100651 | 9/2006 |

(Continued)

OTHER PUBLICATIONS

International Search Report and the Written Opinion dated Jun. 8, 2015 From the International Searching Authority Re. Application No. PCT/IB2014/063632 and Its Translation into English.

(Continued)

*Primary Examiner* — Benjamin J Klein

(57) ABSTRACT

A method to divide liposuction fat into aliquots for use and cryopreservation purposes, the method comprising:

providing a taking container that contains adipose material removed by liposuction, the adipose material including fat and aqueous fluid;

providing a plurality of cryopreservation containers;

taking a quantity of the adipose material from the taking container, keeping the quantity of the adipose material isolated from an external environment; separating by gravity the fat from the aqueous fluid in the adipose material of the taken quantity; and transferring the separated fat into one or more cryopreservation containers, to define isolated aliquots of fat.

8 Claims, 1 Drawing Sheet

(51) Int. Cl.
  *A01N 1/02* (2006.01)
  *C12N 5/077* (2010.01)
  *A61M 1/36* (2006.01)
  *C12N 5/0775* (2010.01)

(52) U.S. Cl.
  CPC ............ *A61M 1/0209* (2013.01); *A61M 1/89* (2021.05); *A61M 1/893* (2021.05); *C12N 5/0653* (2013.01); *A61M 1/3695* (2014.02); *A61M 2202/08* (2013.01); *C12N 5/0662* (2013.01)

(58) Field of Classification Search
  CPC ............ A61M 2202/08; A01N 1/0257; A01N 1/0284; C12N 5/0653; C12N 5/0662
  See application file for complete search history.

(56) References Cited

U.S. PATENT DOCUMENTS

| | | | |
|---|---|---|---|
| 2005/0048033 | A1 | 3/2005 | Fraser et al. |
| 2006/0167401 | A1* | 7/2006 | Cohen .................. A01N 1/0242 604/6.15 |
| 2007/0269887 | A1* | 11/2007 | Coelho ............... A61M 1/0209 435/366 |
| 2008/0014181 | A1* | 1/2008 | Ariff ...................... C12M 45/05 424/93.7 |
| 2012/0305129 | A1* | 12/2012 | Austin ................. A01N 1/0236 141/1 |
| 2013/0123747 | A1* | 5/2013 | Tremolada ............ A61M 19/00 604/506 |
| 2013/0158515 | A1 | 6/2013 | Austen |

FOREIGN PATENT DOCUMENTS

| | | |
|---|---|---|
| WO | WO 2013/111130 | 8/2013 |
| WO | WO 2015/015470 | 2/2015 |

OTHER PUBLICATIONS

Official Action dated May 10, 2018 From the US Patent and Trademark Office Re. U.S. Appl. No. 14/909,467. (12 pages).
Official Action dated Nov. 28, 2018 From the US Patent and Trademark Office Re. U.S. Appl. No. 14/909,467. (8 pages).
Restriction Official Action dated Jan. 10, 2018 From the US Patent and Trademark Office Re. U.S. Appl. No. 14/909,467. (8 pages).

* cited by examiner

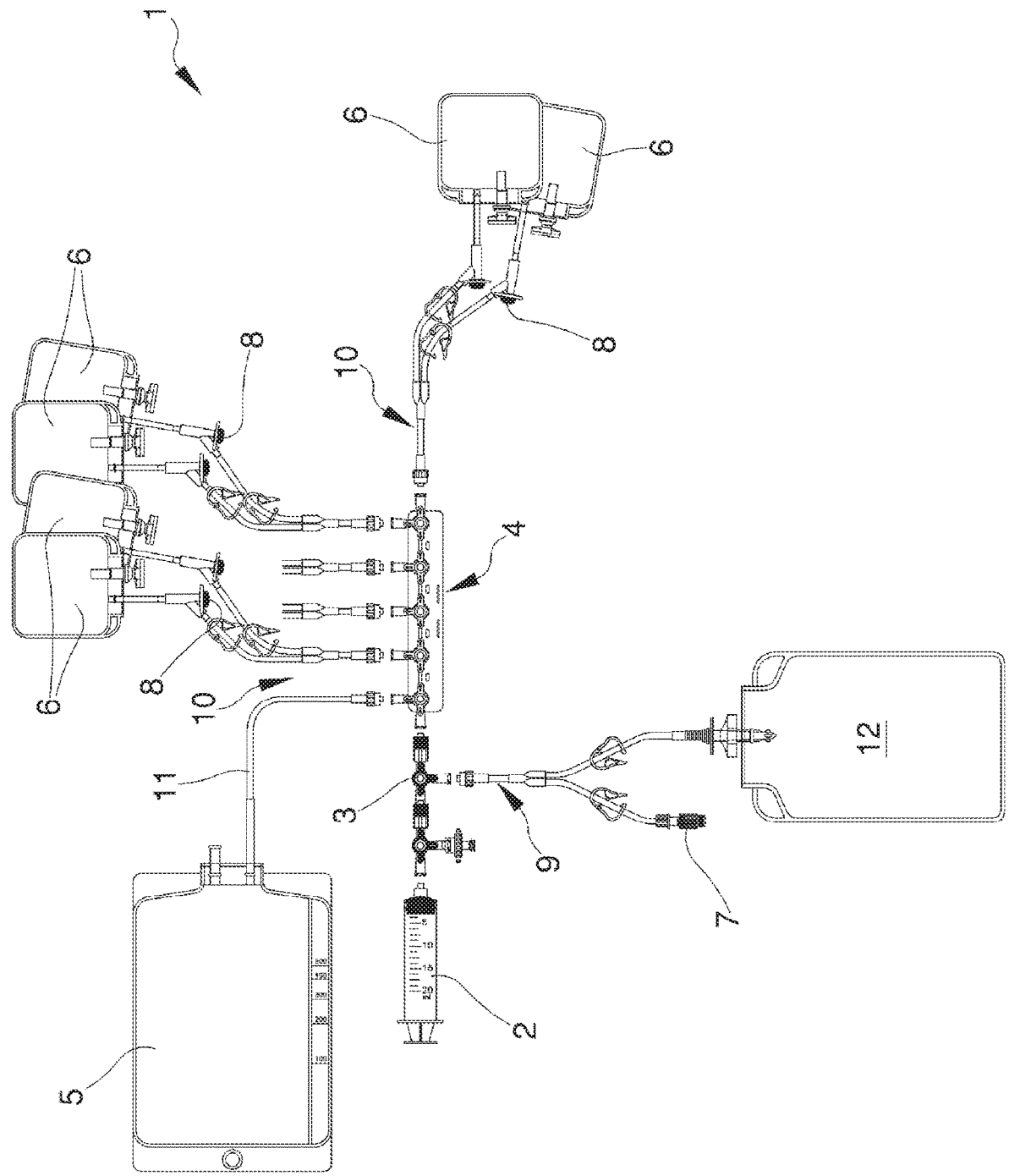

METHOD TO DIVIDE LIPOSUCTION FAT INTO ALIQUOTS TO BE USED AND CRYOPRESERVED

RELATED APPLICATIONS

This application is a Continuation of U.S. patent application Ser. No. 14/909,467 filed on Feb. 2, 2016, which is a National Phase of PCT Patent Application No. PCT/IB2014/063632 having International filing date of Aug. 1, 2014, which claims the benefit of priority of Italian Patent Application No. MO2013A000228 filed on Aug. 2, 2013. The contents of the above applications are all incorporated by reference as if fully set forth herein in their entirety.

FIELD AND BACKGROUND OF THE INVENTION

The present invention relates to a method to divide liposuction fat into aliquots for use and cryopreservation purposes.

The fat removed by means of liposuction is known to be used in the ambit of surgical operations, e.g. for aesthetic and/or regenerative purposes.

Currently, in such operations, the fat is used as soon as removed through the liposuction operation, because there is no way of effectively storing the fat in order to use it when needed, in subsequent times.

This implies that only one part of the fat removed will be employed for the mentioned aesthetic/regenerative operations, while the rest remains unused, and is often disposed of, whereas regenerative operations are particularly effective if repeated over time, even at a distance of years.

It results that, so far, these aesthetic/regenerative operations can be repeated over time only at the price of performing as many liposuction operations, which is not only extremely inefficient, but it is somehow also traumatic and invasive for the person who undergoes them.

SUMMARY OF THE INVENTION

The main aim of the present invention is to provide a method that enable to divide liposuction fat into aliquots, so it can be cryopreserved in order to use it over time for operations of aesthetic and regenerative type.

Within this aim, one object of the invention is to provide a method to divide liposuction fat into aliquots, which process the fat in a bacteriologically isolated manner.

Another object of the present invention is to provide a method to divide liposuction fat into aliquots which allow to overcome the mentioned drawbacks of the prior art in the ambit of a simple, rational, easy and effective to use as well as affordable solution.

The above mentioned objects are achieved by the present method to divide liposuction fat into aliquots for use and cryopreservation purposes, the method comprising:
  providing a taking container that contains adipose material removed by means of liposuction, the adipose material including fat and aqueous fluid;
  providing a plurality of cryopreservation containers;
  taking a quantity of said adipose material from said taking container, keeping said quantity of said adipose material isolated from an external environment;
  separating by gravity the fat from the aqueous fluids in the adipose material of said taken quantity; and
  transferring said separated fat into one or more cryopreservation containers, to define isolated aliquots of fat.

BRIEF DESCRIPTION OF THE SEVERAL VIEW OF THE DRAWINGS

Other characteristics and advantages of the present invention will become better evident from the description of a preferred, but not exclusive embodiment of a system for the performance of method according to the invention, illustrated by way of an indicative, but not limitative example in the enclosed drawings, in which FIG. 1 is a schematic representation of a system for the performance of the method according to the invention.

DESCRIPTION OF SPECIFIC EMBODIMENTS OF THE INVENTION

With particular reference to such FIGURES, globally indicated by reference numeral 1 is a system for dividing liposuction fat into aliquots.

The adipose material containing subcutaneous fat, which remains at the end of an operation of liposuction, is made available in suitable containers, which will hereinafter be referred to as taking containers 12.

In the case of using the so-called "water jet" liposuction method, such material also comprises an aqueous fluid which is substantially formed by the water used in this method, in the form of a pressurized jet, to detach the fat from the surrounding tissues, preparing it for aspiration.

The proposed system 1 comprises at least a transfer circuit 4, 10, 11 able to transfer sealed the adipose material, and also comprises syringe pump 2, 3, connected to said transfer circuit 4, 10, 11, and able to alternately take and contain sealed said adipose material from the taking container 12 and to transfer sealed said fat or said aqueous fluid within said circuit 4, 10, 11.

The syringe pump 2, 3 are available so as to separate by gravity, the fat from the aqueous fluids composing the adipose material contained in them.

The system 1 also provides one or more rejection receptacles 5 connected sealed to the circuit 4, 10, 11, downstream of the syringe pump 2, 3, and able to receive the aqueous fluid, which is a waste for the purposes of the present system 1 (as it will be better clarified hereinafter, when explaining its operation).

Furthermore, the invention provides at least a cryopreservation container 6 (but preferably a plurality) to receive the fat in a sealing manner, which cryopreservation container 6 is connected to the circuit 4, 10, 11 of the proposed system 1, downstream of the syringe pump 2, 3.

This cryopreservation container 6 can be made of a material resistant to a cryoprotective substance (such as in particular dimethyl sulfoxide), for reasons that will be explained hereinafter.

Preferably, the connection between the cryopreservation container 6 and the circuit is of the releasable type.

The circuit also comprises first valve means 4 for allowing alternately the communication between the syringe pump 2, 3 and the rejection receptacle 5 or between the syringe pump and the cryopreservation container 6 (or containers).

The proposed system 1 may further comprise at least one access 7, 8 for the injection of the cryoprotective substance, which access is able to be put in communication with the inside of the cryopreservation container 6.

It should be noticed that the system 1 described above is bacteriologically isolated, since it is able to preserve and process the adipose material (or its components), without this coming into contact with the external environment, thus ensuring the highest level of sterility in particular to the fat that has to be used again for the aforementioned aesthetic and/or reconstructive operations.

Hereinafter, the operation of the invention is illustrated in detail, together with its preferred and not limiting aspects of construction.

As shown in FIG. 1, the aforementioned syringe pump preferably comprise: a pumping syringe 2 and second valve means 3 (e.g. comprising one or more two- or three-way cocks) able to put in sealed communication, alternately, the syringe 2 with the taking container 12 or the syringe 2 with the first valve means 4.

In particular, the second valve means 3 may be connected sealed to an inlet channel 9 having, at the free end thereof, a needle for the introduction of said adipose material.

As said, the adipose material is made available in the taking containers and is preferably "enriched" with mesenchymal cells, especially if the aliquots of fat obtained with the proposed system 1 are to be used in operations of the regenerative type.

The presence of mesenchymal cells is the reason why the invention may provide for the use of the cryoprotective substance and, consequently, of components made of a material resistant to this substance.

In fact, the cryoprotective substance is used to prevent, when the aliquots of fat undergo a significant lowering of temperature, the mesenchymal cells from being damaged by the formation of crystals within the fat itself.

The second valve means 3 are operated so as to be arranged in the configuration wherein they enable the communication between the syringe 2 and the container of adipose material (with the possible interposition of the inlet channel 9).

At this point, the syringe 2 is operated to aspirate inside the adipose material.

Then, the adipose material is left within the syringe 2, which is preferably arranged vertical so that, by virtue of the difference in specific weight between fat and water, the latter deposits at the bottom of its containment barrel, at the so-called "beak".

This operation to be completed can take from fifteen to thirty minutes.

As shown in FIG. 1, the above mentioned first valve means 4 preferably comprise a ramp of three-way cocks, each individually connected either to the rejection receptacle 5 or to at least a respective cryopreservation container 6 (in the example shown the cocks are five in number).

At this point, the first and second valve means 3, 4 are arranged in a respective configuration wherein they only allow communication between the syringe 2 and the rejection receptacle 5, where the water separated from the fat is transferred, as a result of the suitable operation of the syringe 2 itself.

It should be noticed that the rejection receptacle 5 can be connected sealed to the second valve means through a rejection channel 11, included in the circuit.

Once filled with the water to be disposed of, the rejection receptacle 5, which can also be a common drip bag, is removed and replaced.

Then, the second valve means 3 change again their configuration to enable the communication between the syringe 2 and the ramp 4 of three-way cocks, the latter being in turn in a configuration that allows the communication between the cock of the second valve means 3 and the cryopreservation containers 6, while it prevents communication with the rejection receptacle 5.

At this point, the fat contained in the syringe 2, and separated from water, is transferred within the cryopreservation containers 6, to define as many aliquots of fat, usable for the already mentioned operations.

To explain the next operation stage, it is convenient first to describe two devices of the invention which are not necessarily alternative to one another.

According to a first embodiment, the mentioned access for the injection of the cryoprotective substance can be obtained at the outer periphery of each cryopreservation container 6, in which case it is substantially an inlet 8 which can be perforated by the needle of a syringe for injecting the cryoprotective substance, which preferably comprises, or consists of, dimethyl sulfoxide (DMSO).

In the present description, by the term "cryopreservation container" is meant the container in its entirety, and not only the walls that define the inner containment volume (and therefore are included access tangs, ports, etc . . . ).

In addition or as an alternative to this embodiment, an inlet 7 which may be perforated for the injection of dimethyl sulfoxide (or other substance) can be arranged at a further free end of said inlet channel 9, which therefore has a forked configuration as in the representation of FIG. 1, and in practice the second valve means 4 are connected to an access 7 (which may or may not be single) and are configured so as to also allow the sealed communication between the access 7 and the first valve means 3.

In the latter case, not only the channel 9, but also the entire circuit 4, 10, 11 and the syringe pump 2, 3 are made of a dimethyl sulfoxide-resistant material.

Therefore, in practice, in the first embodiment, the DMSO is injected into each container 6, so as to come into contact with the relative aliquot of fat, in order to protect it when the container itself will be stored in a refrigerator (and this is why, as mentioned in a previous paragraph, each container 6 is made of a DMSO-resistant material).

If instead there is a single inlet 7, or any way said inlet 7 is provided at the end of the inlet channel 9, then the user will inject in such inlet 7 the DMSO, which, through the circuit 4, 10, 11 made in the DMSO-resistant material, will reach every single container 6, in order to identify the respective aliquot of fat, able to be refrigerated without damage.

In this manner, instead, each cryopreservation container 6 has internally, completely protected, an aliquot of fat which can be stored in the refrigerator, to define a sort of liposuction fat bank, from which each aliquot can be taken and used when needed, thus overcoming all the drawbacks of prior art.

Preferably, each of these containers 6 is connected to the respective cock of the ramp 4 through a relative outlet channel 10, included in the circuit of the invention.

With the purpose of insulating the aliquot of fat contained in the respective container 6 and separating the latter from the rest of the system 1, this outlet channel 10 is sealed by the user at a given point of its length and then cut according to procedures widely known to the skilled person.

In this way, each container 6 is made individually and can be put into the refrigerator.

According to a possible aspect of the embodiment, each cryopreservation container 6 has, at one of its peripheral walls, a breakable port, in communication with its interior, which can be substantially a closed tang that, following its breaking, allows the outflow of the aliquot of fat for the execution of the operation.

In an alternative embodiment, not shown in the illustrations, the container 6 may be the type of a syringe device connected in a releasable manner to the first valve means 4 and able, alternately, to contain sealed or to inject fat for the infiltrations.

More particularly, this syringe device comprises a receptacle (such as a drip bag) connected in a sealing manner with an infiltration syringe (e.g. through a channel and a single-acting valve incorporated to the syringe itself), to define, as a result of their filling with fat, a portable unit to contain (in isolation), and to inject an aliquot of fat.

After the taking container 12 has been emptied, it is separated from the aforementioned inlet channel 9, at the branch of the aforementioned bifurcation, e.g. through the common practice of sealing and cutting off.

The proposed system 1 is devised to implement the method of the invention, which comprises the stages listed below:
  providing a taking container 12 that contains adipose material removed by means of liposuction (and to which a predefined quantity of mesenchymal cells is preferably added);
  taking a quantity of material from the container, keeping such material isolated from the external environment;
  separating the fat from the aqueous fluids (which as said are substantially made of water) composing the adipose material of the taken quantity; and
  transferring in a sealing manner the separated fat into one or more cryopreservation containers 6, to define as many isolated aliquots of fat.

In a particular embodiment, the method includes the stage of adding a cryoprotective substance to each aliquot of fat, especially in the event of mesenchymal cells being added to the adipose material, for the reasons already explained when describing the system 1.

In this case, the cryopreservation containers 6 are made of a material resistant to a cryoprotective substance (preferably the aforementioned DMSO).

In a further stage of the method, each of said cryopreservation containers 6, which substantially identify respective aliquots of portable fat, is placed in a refrigerator, where the fat is also kept for years without any deterioration.

In practice it has been found how the described invention achieves the intended objects by making available aliquots of liposuction fat, which can be cryopreserved and obtained through the use of a bacteriologically isolated system.

What is claimed is:

1. Method to divide liposuction fat into aliquots for use and cryopreservation purposes, the method comprising:
  providing a taking container that contains adipose material removed by liposuction, the adipose material including fat and aqueous fluid;
  providing a plurality of cryopreservation containers;
  taking a quantity of said adipose material from said taking container, keeping said quantity of said adipose material isolated from an external environment;
  separating by gravity the fat from the aqueous fluid in the adipose material of said taken quantity;
  transferring said separated fat into one or more cryopreservation containers, to define isolated aliquots of fat;
  providing a rejection receptacle and transferring in a sealing manner the separated aqueous fluid into said rejection receptacle;
  providing a syringe pump and operating said syringe pump for assisting in said taking a quantity of said adipose material, said separating by gravity, said transferring the separated fat and said transferring the separated aqueous fluid; and
  providing a transfer circuit, connecting said syringe pump to said transfer circuit and to said taking container, connecting said rejection receptacle to said transfer circuit downstream of said syringe pump, connecting said cryopreservation containers to said transfer circuit downstream of said syringe pump, and operating said syringe pump for assisting in said taking a quantity of said material, said separating by gravity, said transferring the separated fat and said transferring the separated aqueous fluid;
  wherein said transfer circuit comprises first valve means for allowing alternately communication between said syringe pump and said rejection receptacle and between said syringe pump and a said cryopreservation container,
  wherein said syringe pump comprises a pumping syringe and second valve means for allowing alternately communication between said pumping syringe and said taking container and between said pumping syringe and said first valve means, and wherein said first valve means comprise a ramp of three-way cocks, each individually connected either to said rejection receptacle or to a said cryopreservation container;
  wherein the method includes:
  operating said second valve means for putting into communication said pumping syringe with said taking container;
  operating said pumping syringe for assisting in said taking a quantity of the adipose material from said taking container;
  separating by gravity the fat from the aqueous fluid by means of said pumping syringe;
  operating said second valve means for putting into communication said pumping syringe with said first valve means;
  operating said first valve means for putting into communication said pumping syringe with said rejection receptacle;
  operating said pumping syringe for assisting in said transferring the separated aqueous fluid into said rejection receptacle, and
  operating said first valve means for putting into communication said pumping syringe with at least one of said cryopreservation containers for assisting in said transferring the separated fat into said plurality of cryopreservation containers, to define as many isolated aliquots of fat.

2. A method according to claim 1, comprising providing at least one access for the addition of the cryoprotective substance to at least one of said cryopreservation containers wherein a said access is provided at an inlet to said second valve means.

3. A method according to claim 1, wherein a predefined quantity of mesenchymal cells is added to said adipose material.

4. A method according to claim 3, wherein one or more of said cryopreservation containers are made of a material resistant to a cryoprotective substance, and wherein said method comprises adding a cryoprotective substance to each of said aliquots of fat.

5. A method according to claim 4, wherein said cryoprotective substance comprises dimethyl sulfoxide.

6. A method according to claim 4, comprising providing at least one access for the addition of the cryoprotective substance to at least one of said cryopreservation containers.

7. A method according to claim 6, wherein a said access is provided at an inlet to one of said cryopreservation containers.

8. A method according to claim 1, characterized in that each of said cryopreservation containers is put in a refrigerator so that an aliquot of fat is preserved therein.

* * * * *